United States Patent [19]

Buschke

[11] Patent Number: 4,770,636
[45] Date of Patent: Sep. 13, 1988

[54] COGNOMETER

[75] Inventor: Herman Buschke, New York, N.Y.

[73] Assignee: Albert Einstein College of Medicine of Yeshiva University, Bronx, N.Y.

[21] Appl. No.: 36,930

[22] Filed: Apr. 10, 1987

[51] Int. Cl.$^4$ .............................................. G09B 19/00
[52] U.S. Cl. ............................... 434/236; 273/1 GE; 434/365
[58] Field of Search ............. 273/1 GE; 434/236, 365

[56] References Cited

U.S. PATENT DOCUMENTS

Re. 31,070  11/1982  Meyer et al.
4,086,710   5/1978   Craine.
4,193,210   3/1980   Turnquist.
4,340,375   7/1982   Sakaue et al.

OTHER PUBLICATIONS

Controlled Rehearsal and Recall Order in Serial List Retention by H. Buschke and J. V. Hinrichs, Journal of Experimental Psychology, 1968, vol. 78, No. 3, 502–509.
Retention in Immediate Memory Estimated Without Retrieval, Reprinted from Science, Apr. 5, 1963, vol. 140, No. 3562, 56–57.
Utility of Digit Recall Tasks for Assessing Memory in the Aged by T. Crook, S. Ferris, M. McCarthy and D. Rae, Journal of Consulting and Clinical Psychology 1980, vol. 48, No. 2, 228–233.
Contributions to Neuropsychological Assessment, Chap. 3, (Serial Digit Learning), (1983).

Primary Examiner—Leo P. Picard
Attorney, Agent, or Firm—Amster, Rothstein & Ebenstein

[57] ABSTRACT

The cognometer is a portable electronic device programmed for repeated, rapid, automated assessment and monitoring of memory and concentration. The memory monitor randomly generates data and displays the same in a common format, tests the user's comprehension of such data, tests the immediate recall of such data, and tests the delayed recall of such data. The concentration monitor randomly generates a long multi-digit number and displays the same, tests the user's comprehension of such number, and tests the concentration of the user by requiring the user to enter such number while the number is displayed, but without any position cue.

59 Claims, 3 Drawing Sheets

COGNOMETER

BACKGROUND OF THE INVENTION

The present invention relates to a cognometer, and more particularly to a portable electronic cognometer including a memory monitor and a concentration monitor.

Repeated testing of memory and concentration is needed to identify declining cognitive function that may require medical evaluation for dementia, delirium, other medical or psychiatric illness, or the cognitive side-effects of medications. Repeated cognitive monitoring is not commonly carried out even in medical settings, let alone at home, due to lack of a device for automated, eaasily repeated testing.

Easily repeated testing also makes it possible to determine any individual's best (and worst) performance at baseline, so that the individual's memory and concentration in the future can be evaluated by comparison with his or her own previous performance, rather than only by reference to less sensitive general norms obtained from the performance of other more or less similar persons.

Automated testing should provide reliable, rapid, and automatic administration, scoring, and reporting, so that repeated testing can be carried out reliably in precisely the same way as frequently as desired, at home as well as in medical settings. This permits self-testing by the general public, and monitoring of patients with Alzheimer's disease or other cognitive impairment, at home as well as in medical offices, clinics, emergency rooms, hospital wards, psychiatric facilities, or nursing homes.

Tests of memory and concentration should be designed to elicit maximum performance on rigorous but brief and easily repeated tests of sensitive, early, and prominent indicators of cognitive impairment. These tests will be regarded as ecologically valid and appropriate only if they check functions that everyone is expected to be able to perform in ordinary life; for example, everyone is expected to be able to remember a telephone number or copy a sequence of digits. The tests of memory and concentration must require only the simplest of responses, e.g., pressing numbered keys, so that appropriate responses can be obtained from all but the most severely impaired persons. Preferably these tests should be self-paced to compensate for the cognitive slowing often present in aged or cognitively impaired persons. To identify excessive slowing that may be an early indication of impaired cognitive processing, response speed may be measured and reported.

It is essential that such tests measure only the ability in question and not be affected by other considerations. For example, if a person has vision or reading problems which prevent him from seeing or understanding what he does see, his subsequent inability to reproduce a number displayed does not reflect on his memory. Similarly, if he has manual dexterity problems which interfere with his reproducing a displayed number on a keyboard, his failure to key in a number which he was supposed to memorize does not reflect on his memory. Thus it is critical that any cognitive test isolate the cognitive ability being tested and, even if it does not test that ability alone—for other factors always come into play—the test should at least evidence the other factors at play.

Accordingly, it is a object of the present invention to provide a reliable, rapid and automatic administration, scoring and reporting test for self-testing at home or elsewhere.

Another object is to provide such a device which provides for ecologically valid and appropriate testing.

A further object is to provide such a device which effectively isolates for testing the cognitive ability to be tested, even in aged or infirm users.

SUMMARY OF THE INVENTION

It has now been found that the above and related objects of the present invention are obtained in a cognometer comprising a memory monitor and a concetration monitor. The cognometer is an electronic device programmed for repeated, rapid automated assessment and monitoring of both memory and concentration. The cognometer includes means for actuating one of the monitors at a time.

The memory monitor comprises display means, such as a LED or CRT screen, and means for entering data, such as a keyboard. Also provided are means for randomly generating data and displaying the randomly generated data in a common format on the display means, and means for testing the user's comprehension of such randomly generated data. Then, operative only if the user comprehends such randomly generated data, are means for testing the immediate recall by the user of such randomly generated data. Finally, operative only if the user has immediate recall of said such randomly generated data, are means for testing the delayed recall by the user of such randomly generated data.

In a preferred embodiment, the randomly generated data comprises a number comprising a series of digits. The display means displays the series of digits in the common format of a telephone number, preferably a seven-digit number which punctuation intermediate the third and fourth digits or a ten-digit number in the common format of a long distance telephone number—e.g.

"_ _ _ - _ _ _ - _ _ _ _"

or

"(_ _ _) _ _ _ - _ _ _ _".

The data entry means comprises a plurality of numbered buttons.

Preferably the means for testing comprehension of the randomly generated data comprises means for displaying such randomly generated dataon the display means, means for comparing such randomly generated data with first new data entered by the user on the data entry means while such randomly generated data is displayed on the display means and for displaying correct data in the first new data on the display means in alignment with such randomly generated data displayed. Also included are means, operative only if an error was made, either for clearing the display means of any of the data and then restarting the comprehension test means, or for indicating an error was made on the last datum entered by the user on the data entry means and for providing the user another opportunity to enter the correct datum.

Preferably the means for testing the immediate recall of the randomly generated data comprises means for clearing the display means of any of the data while displaying thereon the common format of the randomly generated data. Means display on the display means second new data entered by the user on the data entry means, and means compare such second new data entered by the user with the randomly generated data and draw attention to any errors made by the user. Finally, means, operative only if an error was made, clear the display means of such second new data, and restart the comprehension test means.

Preferably the means for testing the delayed recall of the randomly generated data comprises means for clearning the display means of any of the data displayed and means for distracting the user. Means clear the display means of any of the data displayed while displaying on the display means the common format of the randomly generated data. Means display on the display means third new data entered by the user on the data entry means, and means compare such third new data entered by the user with the randomly generated data. The means for testing delayed recall may additionally comprise means, operative only if an error was made, for restarting the means for testing comprehension. The means for distracting the user may comprise means for requiring the user to correctly copy a series of simple data sets.

The memory monitor additionally includes means for calculating and displaying on the display means a score reflecting the user's performance on the delayed recall testing means. The calculating means divides the number of digits correctly entered by the user as such third new data on the delayed recall test by the total number of digits in the randomly generated number. Preferably the memory monitor includes means for calculating and displaying on the display means scores reflecting the user's performance on the comprehension testing means, the immediate recall testing means and the delayed recall testing means, separately, each of the scoes representing the number of data units correctly entered during each test as a percentage of the total number of data units in the randomly generated data times the number of tests.

A memory monitor with improved scoring additionally includes means for calculating scores reflecting both the number of new data units copied or recalled on each trial and the number of trials needed to copy or recall all of the data units in correct serial order. The calculating means determines scores separately for copying, immediately recall and delayed recall, with each score representing the cumulative number of new data units copied or recalled on each trial up to and including the first completely correct trial, weighted by dividing the number of new data unit of copying, immediate recall or delayed recall by factors taking into account the number of trials needed. The calculating means determines recall scores which take into account any additional copying or immediate recall needed by counting trials from the first copy trial.

The concentration monitor comprises a display means, means for entering data, and means for randomly generating along multi-character data and displaying such randomly generated data on the display means. Means test the user's comprehension of such randomly generated data by requiring the user to enter such randomly generated data on the entering means while displaying such randomly generated data and a position cue on the display means. Means, operative only if the user comprehends such randomly generated data, tests the concentration of the user by requiring the user to enter such randomly generated data on the data entry means while such randomly generated data is displayed on the display means without any position cue and without displaying on the display means the characters already entered. Means, operative only if the user has failed such concentration test, restarts the concentration testing means.

In a preferred embodiment the randomly generated data is a long multi-digit number. The position cue is typically a flashing cursor marking the next character to be copied. The comprehension testing means preferably displays the characters correctly entered by the user in vertical alignment with the corresponding characters of the randomly generated number. The concentration monitor additionally comprises means, operative upon failure of the comprehension test by the user, for relocating the position cue to the beginning of the randomly generated data displayed, and means, operative upon failure of such concentration test, for restarting the copying from the beginning of the randomly generated data without a position cue.

The concentration monitor includes means for calculating and displaying on the display means a score reflecting the user's performance on the comprehension test and on the concentration test, separately, the calculating means determining the score for each of the tests at least in part by dividing the number of characters correctly entered by the user for all trials by the total number of characters in the randomly generated number times the number of trials.

A concentration monitor with improved scoring includes means for calculating scores reflecting both the number of new characters copied with or without a position cue on each trial and the number of trials needed to copy with or without a position cue all of the characters in correct serial order. The calculating means determines scores separately for copying with and without a position cue, with each score representing the cumulative number of new characters copied on each trial up to and including the first completely correct trial, weighted by dividing the number of new characters by factors taking into account the number of trials needed. The calculating means also determines a concentration score which takes into account any additional copying with a position cue needed by counting trial for copying without a position cue from the first copying with a position cue trial.

The present invention further comprises methods of monitoring memory and concentration. The method of monitoring memory comprises the steps of randomly generating data and displaying such randomly generated data in a common format on a display means. The user's comprehension of such randomly generated data is tested and, only if the user comprehends such randomly generated data, the immediate recall by the user of such randomly generated data is tested. Finally, only if the user has immediate recall of such randomly generated data, the delayed recall by the user of such randomly generated data is tested.

The method of monitoring concentration comprises the steps of randomly generating long multi-character data and displaying such randomly generated data on a display means. The user's comprehension of such randomly generated number is tested by requiring the user to enter such randomly generated number on data entry means while displaying such randomly generated number and a position cue on the display means. Only if the user comprehends such randomly generated number, the concentration of the user is tested by requiring the user to enter such randomly generated number on the data entry means while such randomly generated number is displayed on the display means without any position cue. Only if the user has failed such concentration test, the concentration testing is restarted.

BRIEF DESCRIPTION OF THE DRAWING

The above brief description, as well as further objects, features and advantages of the present invention, will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

Figure 1:
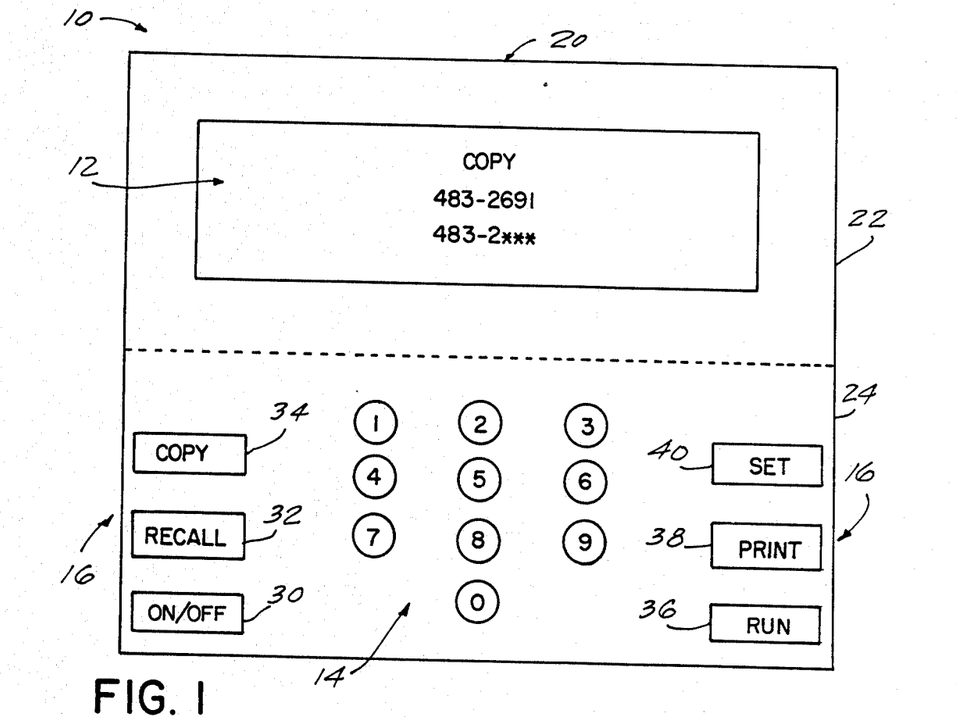
FIG. 1 is a top plan view of a cognometer embodying the principles of the present invention.

Referring now to the drawing, and in particular to FIG. 1 thereof, therein illustrated is a cognometer, generally designated by the reference numeral 10, embodying the principles of the present invention. The cognometer is a small, portable electronic device programmed for repeated, rapid, automated assessment and monitoring of memory and concentration, which are sensitive, early and prominent indicators of cognitive impairment. The cognometer 10 is similar to a small electronic calculator, consisting of an LED or CRT screen, generally generated by the reference numeral 12, to show stimuli (such as numbers and instructions); a set of response keys, generally designated by the reference numeral 14, numbered from 0–9; a set of control keys, generally designated by the reference numeral 16; and microchip firmware (not shown) incorporating the programs for testing memory and concentration. The cognometer's upper face, generally designated by the reference numeral 20, is generally divided into two portions; an upper portion 22 containing the screen 12, and a lower portion 24 containing the response key set 14 and the control key set 16. The plane of the upper portion 22 may be tilted upwardly at an angle to the plane of the lower portion 24 to facilitate reading of the screen 12. The control key set 16 may be disposed in one location or, as illustrated, divided into semi-sets disposed to either side of the response key set 14.

While other embodiments of the present invention may employ alphabetic or alphanumeric response keys, the preferred embodiment illustrated in FIG. 1 utilizes a keyboard of exclusively numeric response keys so that the test results are not affected by education, language, or cultural background because the stimuli and responses are simple digits from 0 through 9. Anyone can read numbers and press numbered keys should be able to use the various tests therein easily, and anyone who can further read the simple control keys should be able to use the cognometer without assistance.

The control key set 16 includes the following keys: beginning at the left side of the cognometer shown in FIG. 1, ON/OFF key 30 (for turning the cognometer on and calling up the initializing or opening program), RECALL and COPY keys 32 and 34 for calling up the memory monitor and concentration monitor programs, respectively; turning now to the right side of the cognometer shown in FIG. 1, RUN key 30 (to start the selected test), PRINT key 38 (to activate an optional paper tape printer to record the test scores), and SET key 40 (to permit the setting of non-default parameters for the selected test).

Figure 2:
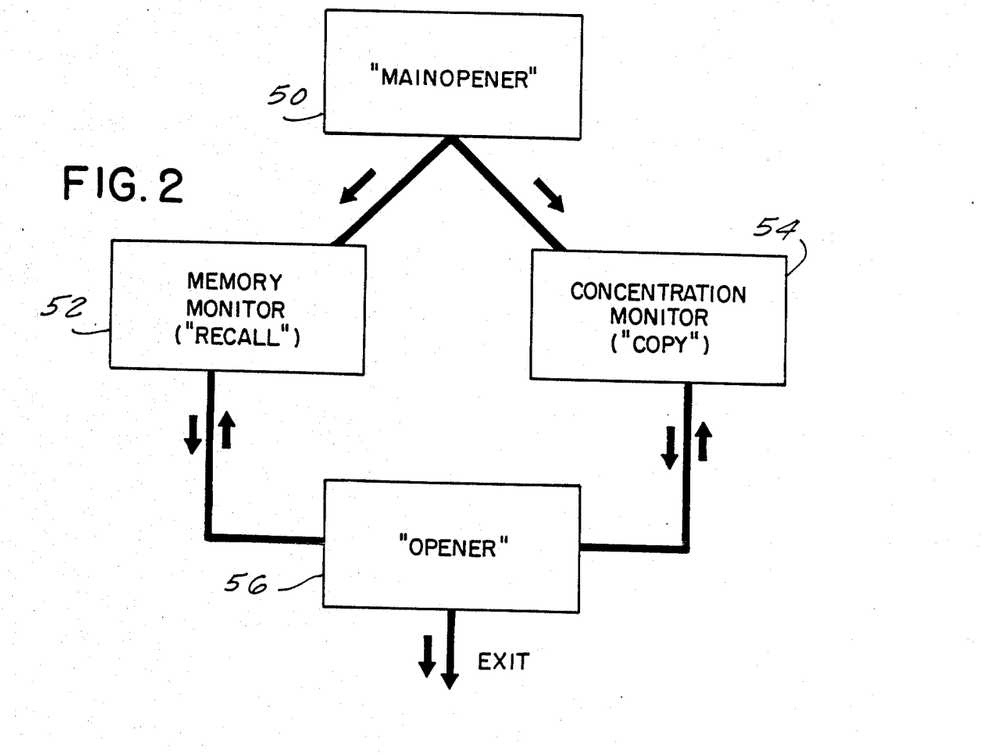
FIG. 2 is an overall flow chart of the operation of the cognometer.

Referring now to FIG. 2 in particular, the software for the cognometer 10 consists of four programs: 1. MAINOPENER, 2. OPENER, 3. MEMORY MONITOR, and 4. CONCENTRATION MONITOR.

When the user actuates the ON/OFF key 30, the "MAINOPENER" program 50 is loaded into memory. The "MAINOPENER" program 50 may provide for entry of data of general utility such as a patient code number identifying the particular patient, his age and the like. Date and time may also be entered in this manner, however, the cognometer itself preferably includes means (i.e., an electronic calendar and clock) for providing this information to the printer. The user can then select either the "MEMORY MONITOR" program 52 or the "CONCENTRATION MONITOR" program 54 by actuating the RECALL key 32 or the COPY key 34, respectively, actuation of the appropriate key causing the appropriate monitor to be loaded into memory. The user then activates the SET key 40 to enter non-default test parameters or the RUN key 36 to start running of the test with default test parameters for all parameters not previously set with the SET key. When the monitor 52, 54 in memory has completed its various tests, the user is turned over to the "OPENER" program 56 which affords him an opportunity to proceed to either of the monitor programs. Thus the user is able to switch back and forth between the memory monitor and concentration monitor programs easily and rapidly. The user can, of course, terminate the session with the cognometer entirely by use of the ON/OFF key 30 or by simply failing to respond to the "OPENER" program 56 for a given period of time (for example, three minutes).

Staged testing, in which each stage must be successfully completed before testing the next stage, is used in both the memory monitor and the concentration monitor. It does not seem reasonable to test immediate recall unless the digits can be copied correctly, or to test delayed recall unless the digits can be recalled without a delay. Therefore, in the memory monitor, immediate recall is not tested until the digits have been copied correctly and delayed recall is not tested until immediate recall is correct. Similarly, in the concentration monitor, copying without a position cue is not tested until all of the digits have been copied correctly with a position cue. Each stage is scored separately, testing all persons when they have met the same criteria for the next stage of testing. Staged testing therefore adjusts the testing procedure to maximize performance at each stage by each individual. Staged testing elicits maximum performance at each stage, induces the processing or controlled learning needed for subsequent stages, and shows that the intended processing or controlled learning has been done, to obtain each individual's best performance on each test.

THE MEMORY MONITOR

Figure 3:
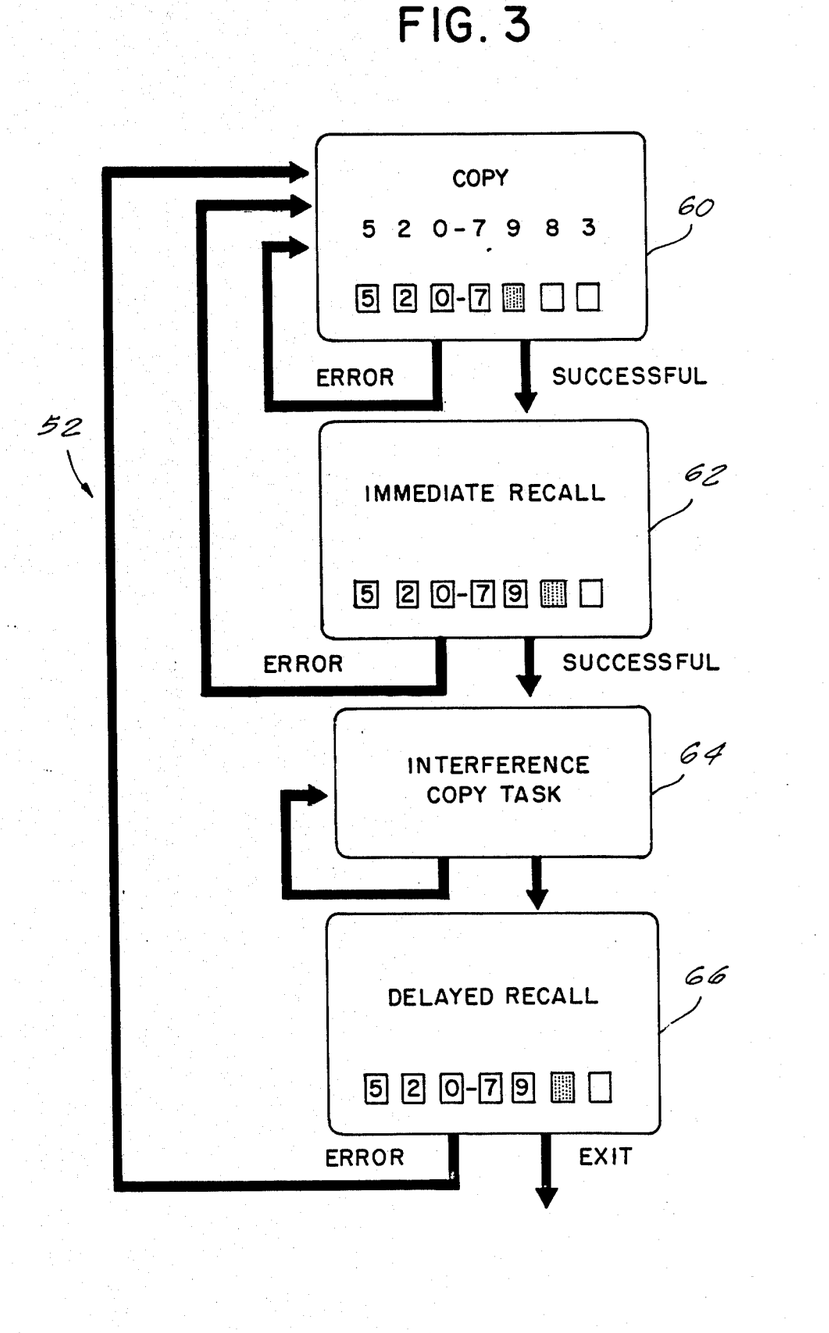
FIG. 3 is a flow chart for the memory monitor.

Referring now in particular to FIG. 3, therein illustrated is a flow chart for the memory monitor program 52. Briefly speaking, the memory monitor is programmed to assess memory and learning by testing delayed recall of a randomly generated 4, 7 or 10 digit number similar to a telephone number. The monitor does this by first randomly generating a number and displaying it on the screen 12, next as shown in box 60 testing the user's comprehension of the number (by requiring him to press the appropriate numbered keys 14 to copy it in serial order while it is displayed on the screen), then as shown in box 62 testing immediate recall of the number (by pressing the appropriate numbered keys when the number disappears from the screen), then as shown in box 64 distracting the user (by requiring him to copy randomly generated two-digit numbers) to obtain delayed recall from secondary memory, and finally as shown in box 66 testing delayed recall of the number (by again requiring him to press the appropriate numbered keys when the number is not on the screen). One delayed recall is sufficient to test memory, but repeated attempts at delayed recall can provide more complete assessment of memory and learning.

Chunking of adjacent elements into fewer multi-item units can make copying and recall easier by reducing the number of units. Because younger persons may be better able to group adjacent digits into a smaller number of units, hyphens are used in the memory monitor to group the digits in the same way for everyone, so that performance by older persons will not be limited by difficulty in grouping. The use of hyphens also results in familiar, ecologically valid telephone numbers which give these tests face validity.

More particularly, as shown in box 60, the memory monitor program shows a randomly generated 4, 7, or 10-digit number on the screen 12, depending on the parameter selected, to be copied into vertically aligned spaces in serial order from left to right by the user pressing the numbered keys 14 corresponding to the digits. Preferably the number to be copied is divided by one or more hyphens, as in a telephone number, depending on the parameter selected. As the user enters each digit, it is shown on the screen immediately below the digit copied; any hyphens are inserted automatically. A flashing crusor also marks the next digit to be copied, as shown in FIG. 3.

When an error occurs, the program will restart the copying process at the beginning of the number (recopy all digits), or will wait for the correct digit to be copied (recopy an individual digit), depending on the parameter selected, or will terminate if the maximum number of copy attempts has been reached.

When the number has been copied to prove comprehension, the screen is cleared and immediately or after a specified number of seconds (1-9), depending on the parameter selected, spaces are shown on the screen for immediate recall of the digits in serial order, as shown in box 62. When an error occurs in immediate recall, the program returns to the copy phase, or terminates if the maximum number of immediate recall attempts has been reached.

When immediate recall is correct, the program provides an interference task to prevent rehearsal, as shown in box 64, by presenting in sequence a series of 01-99 randomly generated two-digit numbers, depending on the parameter selected, to be copied by the user. Each interference item must be copied before the next is shown.

When the interference items have been copied, the program presents spaces on the screen for delayed recall of the number in serial order, as shown in box 66. When an error occurs, the program either returns to the copying phase, or terminates if the maximum number of delayed recall attempts has been reached.

Referring now to Table I, the program scores the test automatically and shows the test scores on the screen. Hard copy can be sent to the printer by use of the print key 38. The printout includes the digits entered by the user, the ratio of the number of correct digits to the total number of digits to be copied or recalled, and the percentage correct on each trial.

A summary score of the percentage correct over all trials up to and including the first 100% correct trial is reported separately for copying, immediate recall, and delayed recall. These summary scores reflect performance both within and over trials, providing convenient and reasonable measures of copying, immediate recall, and delayed recall.

After the score is reported, the "MEMORY MONITOR" program terminates and the "OPENER" program is loaded. Then the user can run the memory monitor again with a new random number, using the same or new parameters, can move to the concentration monitor, or can terminate the session.

The following test parameters can be varied, the recommended default values being underlined:
1. Number of digits to be recalled (4, 7, 10)
2. Hyphens placed as in a phone number (Yes, No)
3. Maximum number of copy attempts (7)
4. When an error occurs, recopy all digits from the start, or correct only the incorrect digit
5. Time delay in seconds between copy and immediate recall (no delay=0)
6. Maximum number of immediate recall attempts (7)
7. Number of two-digit interference items to be copied between immediate and delayed recall (3)
8. Maximum number of delayed recall attempts (4).

Table I shows the scoring of a test of memory for a 7 digit number (168-7805) when 3 attempts at delayed recall were allowed. The digits entered by the user on each attempt are shown on the left side of each line. Copying was repeated until correct on the third attempt, resulting in a copy score of: 3+5+7 correct responses/21 responses (on trials 1-3)=15/21=71%. Immediate recall was not tested until the number was copied correctly. Immediate recall was attempted three times (with repeated copying before each new attempt) before immediate recall was correct, resulting in an immediate recall score of 71%. Delayed recall was not tested until immediate recall was correct. Delayed recall wa attempted three times before delayed recall was correct, resulting in a delayed recall score of 67%. The use of only aa single delayed recall would have resulted in a delayed recall score of 42%. This illustrates that while one delayed recall is sufficient for rapid assessment of memory, repeated attempts at delayed recall provide a more complete assessment of learning.

TABLE I

MEMORY MONITOR

PATIENT: 31
AGE: 99
DATE: 1-17-87
TIME: 11.30
TEST NUMBER: 1
DELAY[0] INTERFERENCE ITEMS [3]
CORRECT NUMBER 169-7805
NUMBER OF TRIALS: 7

| COPY | IMMEDIATE RECALL | DELAYED RECALL |
|---|---|---|
| 169-9000[3/7( 42%)] | | |
| 169-7880[5/7( 71%)] | | |
| 169-7805[7/7(100%)] | 169-9000[3/7 ( 41%)] | |

TABLE I-continued
MEMORY MONITOR

| | | |
|---|---|---|
| 169-7805[7/7(100%)] | 169-7880[5/7 ( 71%)] | |
| 169-7805[7/7(100%)] | 169-7805[7/7 (100%)] | 169-9000[3/7 ( 42%)] |
| 169-7805[7/7(100%)] | 169-7805[7/7 (100%)] | 169-7700[4/7 ( 57%)] |
| 169-7805[7/7(100%)] | 169-7805[7/7 (100%)] | 169-7805[7/7 (100%)] |
| COPY = 71% | IMMEDIATE RECALL = 71% | DELAYED RECALL = 67% |

It will be appreciated that the printout includes the important variable information set by the user: the "time delay" and the number of "interference items" with the "correct number" indicating the number of digits that are to be recalled and whether dividers (e.g., hyphens or hyphens and parentheses) are placed therein as in a phone number. The maximum number of copy, immediate recall and delayed recall attempts are not shown in Table I as the user completed each test within the limit. The only information not indicated is whether, when an error in copying occurred, all digits were copied from the start (the "recopy all digits" default option) or only the incorrect digit was corrected (the "copy last digit" option). If desired, this information too can be included in the print-out.

Various modifications of the basic program can be made without departing the scope of the present invention. For example, instead of displaying a 10-digit number with hyphens between the third and fourth digits and between the sixth and seventh digits to set off the area code and prefix for the telephone number, the first three digits may be enclosed by parentheses and a hyphen used only between the sixth and seventh digits. As another example, the position cue used to indicate the next digit to be entered by the user may be a steady or flashing asterisk, as shown in FIG. 1, an underlining mark, or, if separate rectangles are displayed on the screen for receiving digits entered by the user, a flashing cursor within the next rectangle, as shown in FIG. 3. Clearly a wide variety of alternative position cues may also be used.

Optionally the screen 12 may also contain a space where verbal instructions are displayed to the user. For example, the memory monitor may utilize the instruction "copy" to initiate the comprehension test and the interference activity (of the delayed recall test) and the instruction "recall" to initiate the immediate and delayed recall tests.

Thus, when the user makes an error in his attempt to copy a number, he may be instructed to commence copying over again at the first digit in any one or more of a variety of different ways. For example, the first digit or, if boxes are provided below the number to be copied, the box in which the first digit is to be received may be flashed. Such an animated pictorial is preferred, but depending upon the anticiptated user a verbal instruction such as "start again" may be flashed on the screen over the number to be copied, this instruction appearing either by itself or in combination with a pictorial instruction.

While the interference task is preferably a simple copying task, other tasks sufficient to distract the user and force him to later recall the randomly generated data from long-term memory are suitable. For example, the user may be presented with a series of mathematical tasks such as the addition or subtraction of pairs of one-digit numbers. However such mathematical tasks, as opposed to mere copying tasks, may require mathematical abilities not found in the young, the aged, or the infirm.

In those instances where immediate recall is thee exclusive concern and delayed recall is of no interest (or the testing thereof would be futile), the memory monitor can be terminated after the immediate recall testing.

It will be appreciated that the comprehension test means tests comprehension in a very real way, including not only the ability of the user to recognize the number being displayed, but also his ability to indicate his mental comprehension by the physical act of pressing the correspondingly numbered key 14.

THE CONCENTRATION MONITOR

Figure 4:
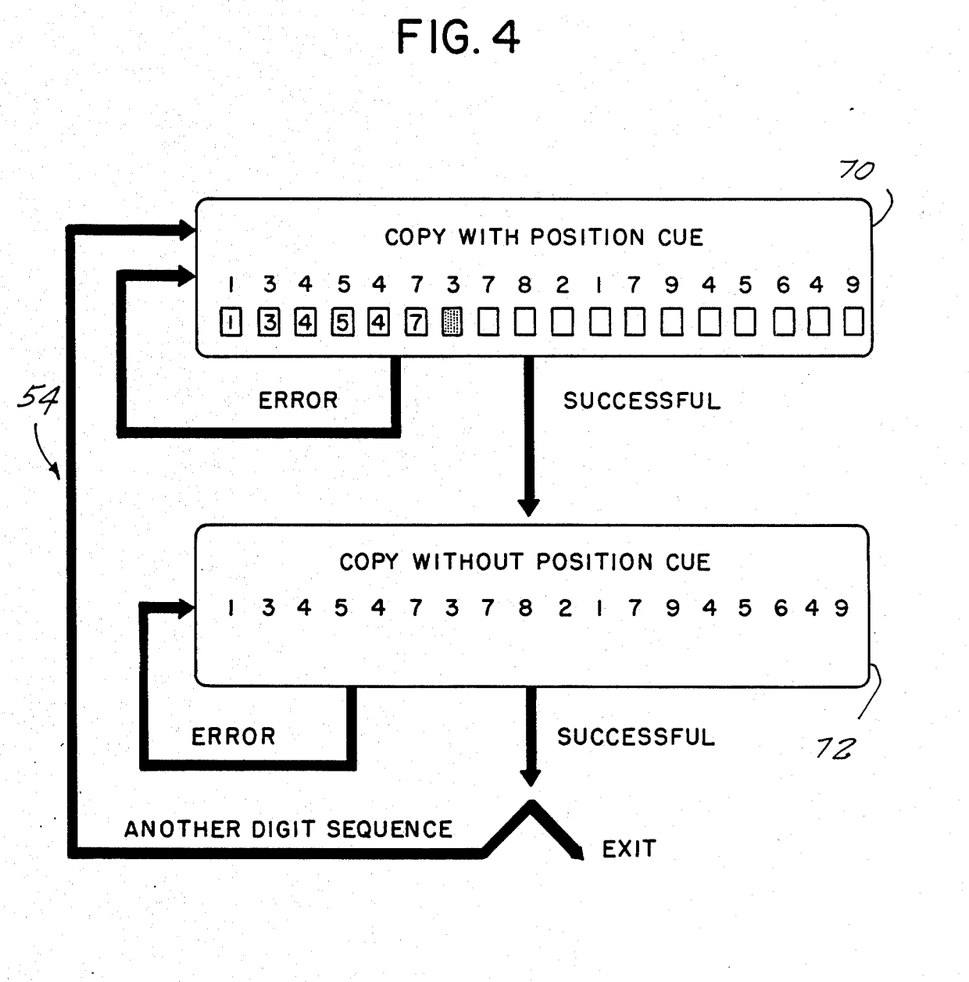
FIG. 4 is a flow chart for the concentration monitor.

Referring now to FIG. 4, the concentration monitor 54, which can be used in conjunction with the memory monitor 52 or by itself to test persons with more severe cognitive impairment, is programmed to test concentration and attention by having the user copy in serial order a randomly generated 9, 18, or 27 digit number. The concentration monitor 54 does this by first randomly generating such a number and displaying it on the screen 12, then, as shown in box 70, testing the user's comprehension of the number by requiring him to show that he can read and copy the digits by copying the number onto the screen with a position cue to mark the next digit to be copied, and finally, as shown in box 72, testing the user's concentration and attention by requiring him to copy the same number without a position cue and without displaying copied digits on the screen.

More particularly, the concentration monitor program shows a randomly generated 9, 18, or 27 digit number on the screen, depending on the parameter selected by the user, an 18-digit number being shown in box 70. As the user enters each digit on numbered keys 14, it is shown on the screen 12 immediaately below the digit copied. A flashing cursor (or asterisk or underlining mark) also provides a position cue to mark the next digit to be copied. When an error occurs, the program restarts the copying test with a position cue at the beginning of the number.

When the number has been copied correctly with a position cue to prove comprehension, the program tests concentration and attention by showing the same number again, as shown in box 72, this time to be copied without a position cue and without showing the digits already copied. When an error occurs, the program restarts the copying without a position cue from the beginning of the number. Copying without a position cue is repeated until the user copies the number correctly (after which another trial may be started with a different number) or the maximum number of attempts is reached.

The program scores the test automatically and shows the test scores on the screen 12. Hard copy can be created on the printer. The report includes the digits entered by the user, the ratio of the number of correctly copied digits to the total number of digits to be copied, and the percentage correct on each trial. A summary score of the percentage correct over all trials, up to and including the first 100% correct trial, is reported separately for copying with a position cue and copying without a position cue. These summary scores reflect performance both within andover trails, providing convenient and reasonable measures of concentration and attention.

As a measure of response speed, the median latency (in milliseconds) between successive keypresses, and the fastest and slowest latencies, are reported for each attempt to copy with or without a position cue.

After the score is reported, the "CONCENTRATION MONITOR" program terminates and the "OPENER" program is loaded. Then the user can run the concentration monitor again with a new random number, using either the same or new parameters, can move to the memory monitor or can terminate the session.

The following test parameters can be varied, the recommended default values being underlined:
1. Number of digits to be copied (9, 18, 27) (any number from 1-35 can be presented)
2. Random sequences using the digits 1-9 equally often, or select particular digits and specify the number of occurrences of each digit.
3. Number of copy attempts with position cue (4)
4. Number of copy attempts without position cue (4).

Table II shows the scoring of a test of concentration in which an 18 digit number (539537911226446878) was to be copied, first with a position cue to mark the next digit to be copied, and then without a position cue. The digits entered by the user on each attempt are shown at the left side of each line. Two attempts were needed to copy the number with a position cue, resulting in a summary score of 12+18 correct responses/18+18 possible (on trials 1 and 2)=30/36=83% correct. Copying without a position cue was not tested until the number was successfully copied with a position cue. Four attempts were needed to copy the number without a position cue, resulting in a summary score of 4+9+15+18 correct responses/18+18+18+18 possible (on trials 3-6)=46/72=63% correct. The numbers at the right side of each line show the median, fastest and slowest latencies between successive keypresses.

It will be appreciated that here too the printout from the concentration monitor includes all of the variable test parameters which the user may have set, except for the number of copy attempts permitted.

In particular instances, as where the user is "put off" or scared by numbers, the concetration monitor may employ randomly generated multi-character data consisting of alphabetical characters rather than digits.

TABLE II

| CONCENTRATION MONITOR | |
|---|---|
| PATIENT: 31 | |
| AGE: 99 | |
| DATE: 1-17-87 | |
| TIME: 11.35 | |
| TEST NUMBER: 2 | |
| NUMBER SIZE 18 | |
| FIXED RANDOM | |
| NUMBERS USED | 1,2,3,4,5,6,7,8,9 |
| OCCURRENCES | 2,2,2,2,2,2,2,2,2 |
| CORRECT ANSWER: 539537911226446878 | |

| COPY WITH POSITION CUE | COPY WITHOUT POSITION CUE |
|---|---|
| 539537911226600000[12/18( 66%)( 753, 355, 2351)] | |
| 539537911226446878[18/18(100%)( 677, 153, 3764)] | |
| | 539550000000000000[4/18( 22%)( 1260, 803, 1648)] |
| | 539537911100000000[9/18( 50%)( 653, 140 1379)] |
| | 539537911226446600[15/18( 83%)( 691, 138 1683)] |
| | 539537911226446878[18/18(100%)( 535, 12, 1911)] |
| WITH POSITION CUE 83% | WITHOUT POSITION CUE 63% |

The simplest measure of performance is the average number or percentage of digits copied or recalled over all trials up to and including the first correct trial, and the scoring system described above (in connection with Tables I and II) employs such a measure. However, this measure does not take into account the number of trials needed or the distribution of performance over successive trials. An improved scoring system for both monitors may be used to take into account both the number of items copied or recalled in correct serial order on each trial and the number of trials needed to copy or recall all of the digits in correct serial order.

To take into account the number of trials needed to copy or recall all digits correctly, performance on successive trials must be weighted in some way that reflects the number of additional trials needed. Furthermore, to score serial order copying or recall it is more appropriate to count the number of new digits copied or recalled for the first time on each trial, rather than all digits copied or recalled on each trial. Repeated serial order copying or recall will always include all previously copied or recalled digits, so that counting all of the digits copied or recalled on each trial would result in repeated credit for previously learned digits that would obscure the copying or recall of new items.

A simple measure of the number of new digits copied or recalled over successive trials can be obtained by counting the number of new digits copied or recalled on each trial, weighting the number of new digits on successive trials to reflect the additional trials, and then summing the weighted number of new digits over all trials up to and including the first trial on which all of the digits are copied or recalled in correct serial order.

The simplest kind of weighting is to divide the number of new items on each trial by the number of that trial (1, 2, 3, etc.). Using this method, the number of new items on trials 1, 2, 3, 4, etc. is divided by 1, 2, 3 and 4, etc., respectively, before summing to obtain the weighted total number of new items copied or recalled over the trials needed. The rationale for this kind of weighting is that the new digits on trial k needed k times as many trials as new digits on trial 1, and therefore should receive only 1/k as much credit.

This weighted sum will be equal to or less than the number of digits to be copied or learned, so that performance can also be summarized by dividing the weighted sum by the number of digits to be copied or recalled to obtain a percentage efficiency score.

This improved scoring procedure takes into account both the number of new digits copied or recalled on each trial and the number of trials needed to copy or recall all of the digits in correct order. When different numbers of trials may be needed to copy or recall all the digits in correct serial order, this procedure provides reasonable and useful summary scores.

In the improved scoring system for the memory monitor, summary scores are reported separately for copying, immediate recall, and delayed recall. Each score is the cumulative number of new items copied or recalled on each trial up to and including the first correct trial, weighted by dividing the number of new items on trials 1, 2, 3, 4, etc. of copying, immediate recall, or delayed recall, by 1, 2, 3, 4, etc. to take into account the number of trials needed. Immediate and delayed recall are then averaged to score total recall. To take into account any additional copying or immediate recall needed, immediate and delayed recall are also scored by counting trials from the first copy(*).

Table III shows a test of memory for a 7-digit number (235-9807) when 4 attempts at delayed recall were allowed. The digits entered by the user on each attempt are shown on the left side of each line. Copying was repeated until correct on the third trial, resulting in a copy score of: 3/1+2/2+2/3 new digits (on trials 1-3)=3+1+0.66=4.66; 4.66/7=66.6%. Immediate recall was not tested until the number was copied correctly. Immediate recall was attempted three times (with repeated copying before each new attempt) before immediate recall was correct, resulting in an immediate recall score (IR) of 66.6%. Delayed recall was not tested until immediate recall was correct. Delayed recall was attempted three times before delayed recall was correct, resulting in a delayed recall score (DR) of 66.6%. Total recall is (IR+DR)/2=133.2/2=66.6%. Scoring IR(*) and DR(*) by weighting based on the number of trials from the first copy trial results in IR(*)=3/3+2/4+2/5=1.9; 1.9/7=27% and DR(*)=3/5+2/6+2/7=1.22; 1.22/7=17%, which take into account the additional trials of copying and immediate recall needed before IR and DR.

TABLE III
MEMORY MONITOR

NAME: 31
AGE: 99
DATE: 321
TIME: 2:50
TEST NUMBER: 1
DELAY[0] INTERFERENCE ITEMS [3]
CORRECT NUMBER: 235-9807
NUMBER OF TRIALS: 7

| COPY | IMMEDIATE RECALL | DELAYED RECALL |
|---|---|---|
| 235-5000[3/7( 43%)] | | |
| 235-9880[5/7( 71%)] | | |
| 235 9807[7/7(100%)] | 235-5000[3/7( 43%)] | |
| 235-9807[7/7(100%)] | 235-9880[5/7( 71%)] | |
| 235-9807[7/7(100%)] | 235-9807[7/7(100%)] | 235-5000[3/7( 43%)] |
| 235-9807[7/7(100%)] | 235-9807[7/7(100%)] | 235-9880[5/7( 71%)] |
| 235-9807[7/7(100%)] | 235-9807[7/7(100%)] | 235-9807[7/7(100%)] |

COPY = 4.6/7 = 66.6%
IR = 4.6/7 = 66.6%
DR = 4.6/7 = 66.6%
TOTAL RECALL = 66.6%
* = 1.9/7 = 27%
* = 1.2/7 = 17%

In the improved scoring system for the concentration monitor, summary scores are reported separately for copying with and without a position cue. Each summary score is the cumulative number of new items copied on each trial up to and including the first completely correct trial, weighted by dividing the number of new items on trials 1, 2, 3, 4, etc. of copying with a position cue or copying without a position cue, by 1, 2, 3, 4, etc. to take into account the number of trials needed. A Cue Ratio is obtained by dividing the score for copying without a position cue by the score for copying with a position cue to assess the relative difficulty of copying without a position cue. To take into account any additional copying with a position cue needed, copying without a position cue is also scored by counting trials from the first trial of copying with a position cue (*).

Table IV shows a test of concentration in which an 18 digit number (938473196862412755) was copied, first with a position cue to mark the next digit to be copied, and then without a position cue. The digits entered by the user on each attempt are shown at the left side of each line. Three trials were needed to copy the number with a position cue, resulting in a summary score of 12/1+3/2+3/3 new digits (on trials 1-3)=12+1.5+1=14.5; 14.5/18=80.5%. Copying without a position cue was not tested until the number was correctly copied with a position cue. Three attempts were needed to copy the number without a position cue (on trials 3-5), resulting in a score of 80.5%. The Cue Ratio=score without cue/score with cue=100%. Scoring of copy without cue (*) by weighting based on the number of trials from the first copy trial results in copy without cue(*)=12/3+3/4+3/5=5.3; 5.3/18=29.7%, which takes into account the additional trials of copying with a cue. The numbers at the right side of each line show the median, fastest and slowest latencies between successive keypresses.

If desired, during entry of the variable parameters, an abbreviated printout may be elected so that the optional printout does not report each individual trial, but only the summary information.

TABLE IV
CONCENTRATION MONITOR

NAME: 31
AGE: 99
DATE: 321
TIME: 2.52
TEST NUMBER: 2
NUMBER SIZE 18
FIXED RANDOM
NUMBERS USED    1 2 3 4 5 6 7 8 9
OCCURENCES      2 2 2 2 2 2 2 2 2
CORRECT ANSWER: 938473196862412755

| COPY WITH POSITION CUE | COPY WITHOUT POSITION CUE |
|---|---|
| 938473196862200000[12/18( 67%)( 732:312-2058)] | |
| 938473196862412200[15/18( 83%)( 642:264-1248)] | |
| 938473196862412755[18/18(100%)( 468:330-1164)] | |
| | 938473196862200000[12/18( 67%)( 624:192-1770)] |
| | 938473196862412200[15/18( 83%)( 618:216-1140)] |
| | 938473196862412755[18/18(100%)( 558:144-1914)] |

WITH POSITION CUE = 14.5/18 = 80.5%
WITHOUT POSITION CUE = 14.5/18 = 80.5%   * = 5.3/18 = 29.7%
CUE RATIO = 100%

Digits are preferably used to test memory and concentration by the cognometer for several reasons. Digits can be used for repeated testing, which is essential for useful monitoring. Generation of randomly ordered digits provides an enormous number of different stimuli for serial order copying or recall, using only a small number of elements that can be presented in many different serial orders. Most of such randomly generated digit sequences will be of a similar degree of difficulty, but a few may be too easy. If desired, the cognometer can be programmed to reject certain kinds of sequences to assure equal difficulty, or pretested random sequences independently shown to be of equal difficulty can be stored in read-only memory and randomly selected for each test.

Other kinds of simple familiar elements, such as letters or mixed sequences containing both letters and digits, can also be used for these tests of memory and concentration. Letters alone are less desirable because they may sometimes be grouped into already known subsequences such as short words or acronyms. This should not be a problem for sequences that contain (alternating) letters and digits. However, the use of letters would require a much more complex keyboard that would make responding unnecessarily difficult for the user.

To summarize, the present invention provides a reliable, rapid and automatic administration, scoring, and reporting test for self-testing at home or elsewhere. The testing is ecologically valid and appropriate and effectively isolates the cognitive ability to be tested, even in aged or infirm users. Testing, scoring, and reporting of results, on screen or by optional printout on paper tape, are fully automatic, so that both monitors can be used for self-testing by the general public and for testing patients at home, as well as for testing by physicians, nurses or other professionals. Each monitor requires only a few moments and is easily repeated at any time by automatic generation of new random numbers. Other easily discriminated symbols, such as letters, can be used to test anyone who does not know numbers.

Now that that the preferred embodiments of the present invention have been shown and described, various modifications and improvements thereon will become readily apparent to those skilled in the art. Accordingly, the spirit and scope of the present invention is to be limited only by the appended claims, and not by the foregoing specification.

What is claimed is:

1. A memory monitor comprising:
   (A) display means;
   (B) means for entering data;
   (C) means for randomly generating data and displaying said randomly generated data is a common format on said display means;
   (D) means for testing the user's comprehension of said randomly generated data;
   (E) means, operative only if the user comprehends said randomly generated data, for testing the immediate recall by the user of said randomly generated data; and
   (F) means, operative only if the user has immediate recall of said randomly generated data, for testing the delayed recall by the user of said randomly generated data.

2. The memory monitor of claim 1 wherein said randomly generated data comprises a number comprising a series of digits.

3. The memory monitor of claim 2 wherein said display means displays said series of digits in the common format of a telephone number.

4. The memory monitor of claim 3 wherein said telephone number is a seven-digit number with punctuation intermediate the third and fourth digits.

5. The memory monitor of claim 3 wherein said telephone number is a ten-digit number in the common format of a long distance telephone number.

6. The memory monitor of claim 5 wherein the common format is

"_ _ _ - _ _ _ - _ _ _ _"

or

"(_ _ _) _ _ _ - _ _ _ _".

7. The memory monitor of claim 2 wherein said data entry means comprises a plurality of numbered buttons.

8. The memory monitor of claim 1 wherein said means for testing comprehension of said randomly generated data comprises means for displaying said randomly generated data on said display means, and means for comparing said randomly generated data with first new data entered by the user on said data entry means while said randomly generated data is displayed on said display means and for displaying correct data in said first new data on said display means in alignment with said randomly generated data displayed.

9. The memory monitor of claim 8 additionally comprising means, operative only if an error was made, for clearing said display means of any of said data and then restarting said comprehension test means.

10. The memory monitor of claim 8 additionally comprising means, operative only if an error was made, for indicating an error was made on the last datum entered by the user on said data entry means and for providing the user another opportunity to enter the correct datum.

11. The memory monitor of claim 1 wherein said means for testing the immediate recall of said randomly generated data comprises means for clearing said display means of any of said data while displaying on said display means the common format of said randomly generated data; means for displaying on said display means second new data entered by the user on said data entry means; means for comparing said second new data entered by the user with said randomly generated data and drawing attention to any errors made by the user; and means, operative only if an error was made, for clearing said display means of said second new data and restarting said comprehension test means.

12. The memory monitor of claim 1 wherein said means for testing the delayed recall of said randomly generated data comprises means for clearing said display means of any of said data displayed; means for distracting the user; means for clearing said display means of any of said data displayed while displaying on said display means the common format of said randomly generated data; means for displaying on said display means third new data entered by the user on said data entry means; and means for comparing said third new data entered by the user with said randomly generated data.

13. The memory monitor of claim 12 wherein said delayed recall test means additionally comprises means, operative only if an error was made, for restarting said comprehension testing means.

14. The memory monitor of claim 12 wherein said means for distracting the user comprises means for requiring the user to correctly copy a series of simple data sets.

15. The memory monitor of claim 12 additionally including means for calculating and displaying on said display means a score reflecting the user's performance on the delayed recall testing means.

16. The memory monitor of claim 15 wherein said calculating means divides the number of digits correctly entered by the user as said third new data on said delayed recall test by the total number of digits in said randomly generated number.

17. The memory monitor of claim 1 additionally including means for calculating and displaying on said display means a score reflecting the user's performance on the delayed recall testing means.

18. The memory monitor of claim 1 additionally including means for calculating and displaying on said display means scores reflecting the user's performance on the comprehension testing means, the immediate recall testing means and the delayed recall testing means, separately, each of said scores representing the number of data units correctly entered during each test as a percentage of the total number of data units in the randomly generated data times the number of tests.

19. The memory monitor of claim 1 additionally including means for calculating scores reflecting both the number of new data units copied or recalled on each trial and the number of trials needed to copy or recall all of the data units in correct serial order.

20. The memory monitor of claim 19 wherein said calculating means determines scores separately for copying, immediately recall and delayed recall, with each score representing the cumulative number of new data units copied or recalled on each trial up to and including the first completely correct trial, weighted by dividing the number of new data units of copying, immediate recall or delayed recall by factors taking into account the number of trials needed.

21. The memory monitor of claim 20 wherein said calculating means determines recall scores which take into account any additional copying or immediate recall needed by counting trials from the first copy trial.

22. A cognometer comprising in combination in a single portable device:
(A) a memory monitor according to claim 1;
(B) a concentration monitor; and
(C) means for actuating one of said monitors at a time.

23. A concentration monitor comprising:
(A) display means;
(B) means for entering data;
(C) means for randomly generating a long multi-character data and displaying said randomly generated data on said display means;
(D) means for testing the user's comprehension of said randomly generated data by requiring the user to enter said randomly generated data on said data entry means while displaying said randomly generated data and a position cue on said display means;
(E) means, operative only if the user comprehends said randomly generated data, for testing the concentration of the user by requiring the user to enter said randomly generated data on said data entry means while said randomly generated data is displayed on said display means without any position cue; and
(F) means, operative only if the user has failed such concentration test, for restarting the concentration testing means.

24. The concentration monitor of claim 23 wherein said position cue is a flashing cursor marking the next character to be copied.

25. The concentration monitor of claim 23 additionally comprising means, operative upon failure of such comprehension test by the user, for relocating said position cue to the beginning of said randomly generated data displayed.

26. The concentration monitor of claim 23 additionally comprising means, operative upon failure of said concentration test, for restarting the copying from the beginning of said randomly generated data without a position cue.

27. The concentration monitor of claim 23 wherein said concentration testing means compares said characters entered by said user with the characters of said randomly generated data without displaying on said display means the characters already entered.

28. The concentration monitor of claim 23 wherein said comprehension testing means displays correctly entered characters on said display means in vertical alignment with the corresponding characters in said randomly generated data.

29. The concentration monitor of claim 23 additionally including means for calculating and displaying on said display means a score reflecting the user's performance.

30. The concentration monitor of claim 29 including means for calculating and displaying on said display means a score reflecting the user's performance on the comprehension test and on the concentration test, separately, said calculating means determining said score for each of said tests at least in part by dividing the number of characters correctly entered by the user for all trials by the total number of characters in said randomly generated data in said trials.

31. The concentration monitor of claim 23 additionally including means for calculating scores reflecting both the number of new characters copied with or without a position cue on each trial and the number of trials needed to copy with or without a position cue all of the correct characters in correct serial order.

32. The concentration monitor of claim 31 wherein said calculating means determines scores separately for copying with and without a position cue, with each score representing the cumulative number of new characters copied on each trial up to and including the first completely correct trial, weighted by dividing the number of new characters by factors taking into account the number of trials needed.

33. The concentration monitor of claim 32 wherein said calculating means determines a concentration score which takes into account any additional copying with a position cue needed by counting trials for copying without a position cue from the first copying with a position cue trial.

34. The concentration monitor of claim 23 where said randomly generated data is a long multi-digit number.

35. A cognometer comprising in combination in a single portable device:
(A) a memory monitor;
(B) a concentration monitor according to claim 23; and
(C) means for actuating one of said monitors at a time.

36. A method of monitoring memory comprising the steps of:
(A) randomly generating data and displaying said randomly generated data in a common format on a display means;
(B) testing the user's comprehension of said randomly generated data;
(C) only if the user comprehends said randomly generated data, testing the immediate recall by the user of said randomly generated data; and
(D) only if the user has immediate recall of said randomly generated data, testing the delayed recall by the user of said randomly generated data.

37. A memory monitor comprising:
(A) display means;
(B) means for entering data;
(C) means for randomly generating data and displaying said randomly generated data in a common format on said display means;
(D) means for testing the user's comprehension of said randomly generated data; and
(E) means, operative only if the user comprehends said randomly generated data, for testing the immediate recall by the user of said randomly generated data.

38. The memory monitor of claim 37 wherein said randomly generated data comprises a number comprising a series of digits.

39. The memory monitor of claim 38 wherein said display means displays said series of digits in the common format of a telephone number.

40. The memory monitor of claim 39 wherein said telephone number is a seven-digit number with punctuation intermediate the third and fourth digits.

41. The memory monitor of claim 39 wherein said telephone number is a ten-digit number in the common format of a long distance telephone number.

42. The memory monitor of claim 41 wherein the common format is

"_ _ _ - _ _ _ - _ _ _ _"

or

"(_ _ _) _ _ _ - _ _ _ _".

43. The memory monitor of claim 38 wherein said data entry means comprises a plurality of numbered buttons.

44. The memory monitor of claim 37 wherein said means for testing comprehension of said randomly generated data comprises means for displaying said randomly generated data on said display means, and means for comparing said randomly generated data with first new data entered by the user on said data entry means while said randomly generated data is displayed on said display means and for displaying correct data in said first new data on said display means in alignment with said randomly generated data displayed.

45. The memory monitor of claim 44 additionally comprising means, operative only if an error was made, for clearing said display means of any of said data and then restarting said comprehension test means.

46. The memory monitor of claim 44 additionally comprising means, operative only if an error was made, for indicating an error was made on the last datum entered by the user on said data entry means and for providing the user another opportunity to enter the correct datum.

47. The memory monitor of claim 37 wherein said means for testing the immediate recall of said randomly generated data comprises means for clearing said display means of any of said data while displaying on said display means the common format of said randomly generated data; means for displaying on said display means second new data entered by the user on said data entry means; means for comparing said second new data entered by the user with said randomly generated data and drawing attention to any errors made by the user; and means, operative only if an error was made, for clearing said display means of said second new data and restarting said comprehension test means.

48. The memory monitor of claim 47 additionally including means for calculating and displaying on said display means a score reflecting the user's performance on the immediate recall testing means.

49. The memory monitor of claim 48 wherein said calculating means divides the number of digits correctly entered by the user as said second new data on said immediate recall test by the total number of digits in said randomly generated number.

50. The memory monitor of claim 37 additionally including means for calculating and displaying on said display means a score reflecting the user's performance on the immediate recall testing means.

51. The memory monitor of claim 37 additionally including means for calculating and displaying on said display means scores reflecting the user's performance on the comprehension testing means and the immediate recall testing means, separately, each of said scores representing the number of data units correctly entered during each test as a percentage of the total number of data units in the randomly generated data times the number of tests.

52. The memory monitor of claim 37 additionally including means for calculating scores reflecting both the number of new data units copied or recalled on each trial and the number of trials needed to copy or recall all of the data units in correct serial order.

53. The memory monitor of claim 52 wherein said calculating means determines scores separately for copying and immediately recall, with each score representing the cumulative number of new data units copied or recalled on each trial up to and including the first completely correct trial, weighted by dividing the number of new data units of copying or immediate recall by factors taking into account the number of trials needed.

54. The memory monitor of claim 53 wherein said calculating means determines recall scores which take into account any additional copying needed by counting trials from the first copy trial.

55. A cognometer comprising in combination in a single portable device:
(A) a memory monitor according to claim 37;
(B) a concentration monitor; and
(C) means for actuating one of said monitors at a time.

56. A method of monitoring concentration comprising the steps of:
(A) randomly generating a long multi-character data and displaying said randomly generated data on a display means;
(B) testing the user's comprehension of said randomly generated data by requiring the user to enter said randomly generated data on data entry means while displaying said randomly generated data and a position cue on the display means;
(C) only if the user comprehends said randomly generated data, testing the concentration of the user by requiring the user to enter said randomly generated data on the data entry means while said randomly generated data is displayed on the display means without any position cue; and
(D) only if the user has failed such concentration test, restarting the concentration testing.

57. A memory monitor comprising:
(A) display means;
(B) means for entering data;
(C) means for generating data and displaying said generated data in a common format on said display means;
(D) means for testing the user's comprehension of said generated data; and
(E) means, operative only if the user comprehends said generated data, for testing the immediate recall by the user of said generated data.

58. The memory monitor of claim 57 additionally including means, operative only if the user has immediate recall of said generated data, for testing the delayed recall by the user of said generated data.

59. A method of monitoring memory comprising the steps of:
(A) generating data and displaying said generated data in a common format on a display means;
(B) testing the user's comprehension of said generated data;
(C) only if the user comprehends said generated data, testing the immediate recall by the user of said generated data; and
(D) only if the user has immediate recall of said generated data, testing the delayed recall by the user of said generated data.

* * * * *